United States Patent [19]

Schmidt et al.

[11] Patent Number: 5,618,832
[45] Date of Patent: Apr. 8, 1997

[54] PRESERVATION OF COLUMN MATERIALS IN AQUEOUS SOLUTIONS

[75] Inventors: Axel Schmidt, Munich; Helmgard Gauhl, Tutzing, both of Germany

[73] Assignee: Boehringer Mannheim GmbH, Mannheim, Germany

[21] Appl. No.: 370,579

[22] Filed: Dec. 20, 1994

[30] Foreign Application Priority Data

Dec. 24, 1993 [DE] Germany ............ 43 44 549.7

[51] Int. Cl.⁶ ............ A01N 43/32; A01N 43/80
[52] U.S. Cl. ............ 514/372; 514/452
[58] Field of Search ............ 514/372, 452

[56] References Cited

U.S. PATENT DOCUMENTS

| | | | |
|---|---|---|---|
| 4,906,651 | 3/1990 | Hsu | 514/372 |
| 5,300,424 | 4/1994 | Hoss et al. | 435/7.1 |

FOREIGN PATENT DOCUMENTS 398795  11/1990  European Pat. Off. .

OTHER PUBLICATIONS

Derwent Publications Ltd., AN 90–345639/46 & JP a–2–250 805 Oct. 8, 1990.
Journal of Chromatography, BD 469, 1989, "Determination of Preservatives in Cosmetic Products" De Kruijf et al.
Varian Instrument Application, BD 11, NR. 3, 1977 "Preserving Liquid Chromatographic Column Life", B. Wadsworth.

*Primary Examiner*—Allen J. Robinson
*Attorney, Agent, or Firm*—Felfe & Lynch

[57] ABSTRACT

Combination composed of 2-methyl-4-isothiazolin-3-one hydrochloride and 5-bromo-5-nitro-1,3-dioxane for the elimination of microbes as well as for the preservation of column materials in aqueous solutions. The biocidal mixture is preferably added at concentrations of 0.001 to 0.3% (w/v).

14 Claims, No Drawings

PRESERVATION OF COLUMN MATERIALS IN AQUEOUS SOLUTIONS

The invention concerns the use of a mixture of methylisothiazolone and bromonitrodioxane for preserving column materials in aqueous solutions.

Column materials in aqueous solutions are mainly used to isolate water-soluble organic compounds such as proteins, nucleic acids and carbohydrates. These compounds promote the growth of microorganisms. Although it is endeavoured to remove residues of organic compounds from the column material as far as possible by rinsing with aqueous solutions, this is often not achieved completely. The column materials contaminated in this way are an ideal nutrient medium for many different microorganisms so that strong microbial contamination can already be observed within a few days.

Microbial contamination of column materials adversely affects the re-use of the materials, which are often very expensive. This manifests itself in the form of poor separation efficiency and/or flow rate, contamination of the column material by metabolic products of the microorganisms, damage to the products to be separated e.g. degradation of proteins and nucleic acids, and in some cases the column materials themselves may even be attacked by microbial contamination. Microbial growth on column materials is therefore usually prevented by the addition of biocidal solvents such as alcohol or highly-concentrated salt solutions, to the separation material. Other known measures for preventing microbial growth are to adjust the pH value to either strongly alkaline (>12) or strongly acidic (<2) values or to add sodium azide (B. Wadsworth, Varian Instrum. Appl. Vol. 11/3, p. 10 (1977)).

However, all known measures to prevent microbial growth have inherent disadvantages. Thus organic solvents have to be added at high concentrations (about 15–30% v/v). In addition some of them are difficult to degrade and they therefore pollute the environment. Moreover a disadvantage of organic solvents is that they damage some column materials. High salt concentrations can lead to undesired crystallization of the salts on the column materials. In addition, the salt load considerably pollutes the environment during washing. Storage at high or low pH values is hazardous and is not tolerated by many column materials. Sodium azide is highly toxic and mutagenic (Buchberger and Kiermeier, Clin. Chem. 25, p. 1514–5 (1979); Dangerous Properties of Industrial Materials Report Vol. 10/6, p. 65–76 (1990)). In addition sodium azide can form highly explosive complexes with heavy metals. Moreover, the microbial efficacy of sodium azide depends on the pH and is very weak. Some microorganisms can even utilize the azide salt as a nutrient (i.e., they are resistant to it).

The underlying object of the invention is therefore to eliminate the abovementioned disadvantages in the preservation of column materials in aqueous solutions.

The object is achieved by the use of a combination a mixture of 2-methyl-4-isothiazolin-3-one hydrochloride (methyliso-thiazolone) and 5-bromo-5-nitro-1,3-dioxane (bromonitrodioxane) which effectively protects the column materials against microbial contamination even at very low concentrations. Moreover the mixture can also be used advantageously for column materials which are already strongly contaminated with microbes, enabling the microorganisms load to be significantly reduced within a few days.

The mixture according to the invention preferably consists of methylisothiazolone and bromonitrodioxane in approximately equal portions. However, mixtures consisting of methylisothiazolone and bromonitrodioxane in a ratio of 20:80 to 80:20 also inhibit microbial growth. The mixtures composed of two components suppress microbial growth even when they are added at concentrations of as little as 0.001% (w/v) to the aqueous column material. A concentration of about 0.05% to 0.3% (w/v) is preferably used. 0.1% (w/v) of a 1:1 mixture of methylisothiazolone/bromonitrodioxane has proven to be particularly advantageous for the inhibition of microbial growth in column materials. Furthermore the biocide mixture is effective over an extended time period (months to years), it is practically non-toxic and readily degradable i.e. environmentally compatible, it does not damage the column materials and can easily be separated from these by simple washing.

The biocide mixture according to the invention is suitable for the preservation of chemically different column materials. All materials which are suitable for columnar separation in aqueous systems such as for example Sepharose, Sephadex, agarose, acrylic gels, polystyrenes, gels based on silicates and so forth, may be treated. In this connection it is unimportant whether the polymers are coated with affinity ligands or carry charges.

The biocide combination according to the invention can also be used to reduce microbial infestation of column materials that are already strongly contaminated with microbes (e.g. $10^6$ to $10^8$ microbes/ml) and significantly reduces the number of organisms after only few days (e.g 2 days at, 28° C.). In some cases complete freedom from germs has been achieved.

2-methyl-4-isothiazolin-3-one hydrochloride and 5-bromo-5-nitro-1, 3-dioxane have already been known for a long time as substances and are commercially available from various companies (e.g. Boehringer Mannheim under the trade names MIT or bromonitrodioxane, Bronidox K). The substances are used e.g. as highly effective biocides in cosmetics as well as in some technical products (see e.g. "Praxis der Sterilisation, Desinfection-Konservierun", Karl-Heinz Wallhäuβer, 4th Edition, Georg Thieme Verlag Stuttgart/New York, p. 445 and 534, 1988). Moreover the combination of these compounds and their use as preservatives in diagnostic tests are known See e.g., European Patent Application 467,337, now U.S. Pat. No. 5,300,424, incorporated by reference.

The fact that this mixture composed of methylisothiazolone and bromonitrodioxane has a substantial biocidal effect on column materials in aqueous solutions is surprising, since in contrast to the use of the conventional solutions in diagnostics, adsorptive effects can occur in column materials thus lowering the efficacy of biocides. Thus other known substances with a biocidal efficacy to not result in a reduction in the number of microbes.

The invention is exemplified by the following:

EXAMPLE

Biocide mixture used: methylisothiazolone/bromonitrodioxane (9 g MIT and 10 g Bronidox K/100 ml ethanol, 96%)
Microbially-contaminated sample material:
1) G-gel
2) protein A-Sepharose (stored for 60 hours in water at room temperature)
3) protein A-sepharose (stored for 60 hours in 10 mM K-phosphate buffer pH 7.5 at room temperature)
4) DEAE-Sepharose
5) Q-Sepharose
6) Immobilized streptavidin in 20 mM phosphate buffer, 0.15 M NaCl, 0.05% sodium azide Pre-Treatment
0.75 g of each of the samples 1), 4) and 5) were weighed, suspended in 3 ml sterile 0.85% saline solution and processed further as in the other samples, which follow. Note that samples "2", "3" and "6" require pretreatment, as these are already in solution.

Sample 3) must be diluted in a ratio of 4+1 since it cannot otherwise be pipetted.

The respective initial microorganism titre was determined in the prepared samples before dividing each of them into 3×1 ml (in order to be able to test 3 different biocide mixture solutions) by plating out on standard 1 nutrient agar and incubating at 28°C. This medium contains the nutrients most important to microorganism growth, including 15 g of peptide, 3 g yeast extract, 6 g sodium chloride, and 1 g glucose.

The biocide mixture was added to the divided samples at a final concentration of 0.01–0.04 and 0.1% (w/v), incubated at 28°C. to allow it to take effect and the remaining microbial titre was subsequently determined as described above.

Number of Organisms Determined in CFU/ml

| | | Addition of biocide mixture | | |
|---|---|---|---|---|
| Sample | Initial titre | 0.01% | 0.04% | 0.1% |
| 1) | >10log7 | unchanged | 0 | 0 |
| 2) | 1.2 × 10log6 | 1.1 × 10log4 | 4.1 × 10log4 | 1.4 × 10log4 |
| 3) | 1.3 × 10log7 | 1.3 × 10log7 | 8.8 × 10log4 | 0 |
| 4) | 8.0 × 10log7 | 8.0 × 10log7 | 6.0 × 10log4 | 2.0 × 10log2 |
| 5) | 8.0 × 10log7 | 8.0 × 10log7 | 9.3 × 10log5 | 4.6 × 10log4 |
| 6) | >10log7 | unchanged | unchanged | unchanged |

In the case of Sample 1, the 0.01% biocide caused no change, and thus additional biocide was necessary to have an effect. At 0.04%, note the strong response. Sample 6, as noted, supra, contains a preservation reagent. It is intended as a comparison example, and indicates that additional components should not be used for maximum effect to be achieved.

It will be understood that the specification and examples are illustrative but not limitative of the present invention and that other embodiments within the spirit and scope of the invention will suggest themselves to those skilled in the art.

We claim:

1. A composition of matter comprising:
   a separation column; and
   a solution in contact with said separation column, said solution containing a combination of 2-methyl-4-isothiazolin-3-one hydrochloride and 5-bromo-5-nitro-1,3-dioxane, in amounts synergistic such that the solution is biocidally effective.

2. The composition of claim 1, wherein said 2-methyl-4-isothiazolin-3-one hydrochloride and 5-bromo-5-nitro-1,3-dioxane are present at a ratio of about 1:1 and at a concentration of from about 0.001% to about 0.3% (w/v).

3. The composition of claim 1, wherein said solution is an aqueous solution.

4. The composition of claim 3, wherein said 2-methyl-4-isothiazolin-3-one hydrochloride and 5-bromo-5-nitro-1,3-dioxane are present at a concentration of about 0.1% (w/v).

5. The composition according to claim 1, wherein said separation column contains material selected from the group consisting of G-gel, protein A-Sepharose, DEAE Sepharose, and Q-Sepharose.

6. The invention according to claim 1 wherein said 2-methyl-4-isothiazolin-3-one hydrochloride and said 5-bromo-5-nitro-1,3-dioxane are present in said solution in a ratio of from 20:80 to 80:20.

7. A method for preserving a separation column comprising immersing said column in an aqueous solution comprising 2-methyl-4-isothiazolin-3-one hydrochloride and 5-bromo-5-nitro-1,3-dioxane both present in said aqueous solution in synergistic amount such that the aqueous solution is biocidally active.

8. The method of claim 7 wherein said separation column contains material selected from the group consisting of G-gel, protein A-Sepharose, DEAE Sepharose, and Q-Sepharose.

9. The method of claim 7 wherein said 2-methyl-4-isothiazolin-3-one hydrochloride and 5-bromo-5-nitro-1,3-dioxane being present in a ratio of about 1:1.

10. The method of claim 7, wherein said 2-methyl-4-isothiazolin-3-one hydrochloride and said 5-bromo-5-nitro-1,3-dioxane are present in said solution in a ratio of from 20:80 to 80:20.

11. A method for elimination of microbes in a separation column comprising contacting said separation column with an aqueous solution comprising 2-methyl-4-isothiazolin-3-one hydrochloride and 5-bromo-5-nitro-1,3dioxane both present in said aqueous solution in synergistic amounts such that the aqueous solution is biocidally active for a microbiocidally effective amount of time.

12. The method of claim 11 wherein said separation column contains material selected from the group consisting of G-gel, protein A-Sepharose, DEAE Sepharose, and Q-Sepharose.

13. The method of claim 11 wherein, said 2-methyl-4-isothiazolin-3-one hydrochloride and 5-bromo-5-nitro-1,3-dioxane being present in a ratio of about 1:1.

14. The method of claim 11, wherein said 2-methyl-4-isothiazolin-3-one hydrochloride and said 5-bromo-5-nitro-1,3dioxane are present in said solution in a ratio of from 20:80 to 80:20.

* * * * *

UNITED STATES PATENT AND TRADEMARK OFFICE
CERTIFICATE OF CORRECTION

PATENT NO. : 5,618,832
DATED : April 8, 1997
INVENTOR(S) : Schmidt et al.

It is certified that error appears in the above-identified patent and that said Letters Patent is hereby corrected as shown below:

IN COLUMN 3, LINE 46, delete the phrase "amounts synergistic" and replace with --synergistic amounts--.

Signed and Sealed this

Eleventh Day of May, 1999

Attest:

Q. TODD DICKINSON

Attesting Officer  Acting Commissioner of Patents and Trademarks